United States Patent
Ellman

(10) Patent No.: US 8,992,524 B1
(45) Date of Patent: Mar. 31, 2015

(54) ELECTROSURGICAL COBB ELEVATOR INSTRUMENT

(76) Inventor: Alan G. Ellman, Baldwin, NY (US)

( * ) Notice: Subject to any disclaimer, the term of this patent is extended or adjusted under 35 U.S.C. 154(b) by 1002 days.

(21) Appl. No.: 12/924,819

(22) Filed: Oct. 7, 2010

(51) Int. Cl.
*A61B 18/14* (2006.01)
*A61B 18/00* (2006.01)

(52) U.S. Cl.
CPC ............... *A61B 18/14* (2013.01); *A61B 18/148* (2013.01); *A61B 2018/00565* (2013.01); *A61B 2018/00607* (2013.01); *A61B 2018/142* (2013.01)
USPC .................................. 606/45; 606/41; 606/49

(58) Field of Classification Search
CPC ............... A61B 2018/142; A61B 2018/00976; A61B 2018/00339; A61B 2018/00565; A61B 2018/0097; A61B 2018/1253
USPC .......................................................... 606/45
See application file for complete search history.

(56) References Cited

U.S. PATENT DOCUMENTS

| 6,530,924 B1* | 3/2003 | Ellman et al. ................... 606/45 |
| 2002/0045895 A1* | 4/2002 | Sliwa et al. ..................... 606/41 |
| 2003/0195504 A1* | 10/2003 | Tallarida et al. ................ 606/41 |
| 2004/0138527 A1* | 7/2004 | Bonner et al. ................ 600/114 |
| 2006/0178668 A1* | 8/2006 | Albritton, IV ................. 606/45 |
| 2009/0069802 A1 | 3/2009 | Garito et al. |

FOREIGN PATENT DOCUMENTS

| JP | 2001087274 | 3/2001 |
| JP | 2005328917 | 2/2005 |

* cited by examiner

*Primary Examiner* — Jaymi Della

(57) ABSTRACT

An electrosurgical Cobb elevator instrument, a soft tissue dissection and/or retraction tool, can be used with and without suction, and is capable of delivering monopolar or bipolar RF energy for cutting and coagulating soft tissue. The device is capable of footswitch or handswitch activation. The tool has a spoon-shaped edge that is preferably sharp to provide blunt dissection in addition to the energy-driven dissection. The instrument of the invention could be used in any procedure that requires soft tissue dissection and/or coagulation.

8 Claims, 2 Drawing Sheets

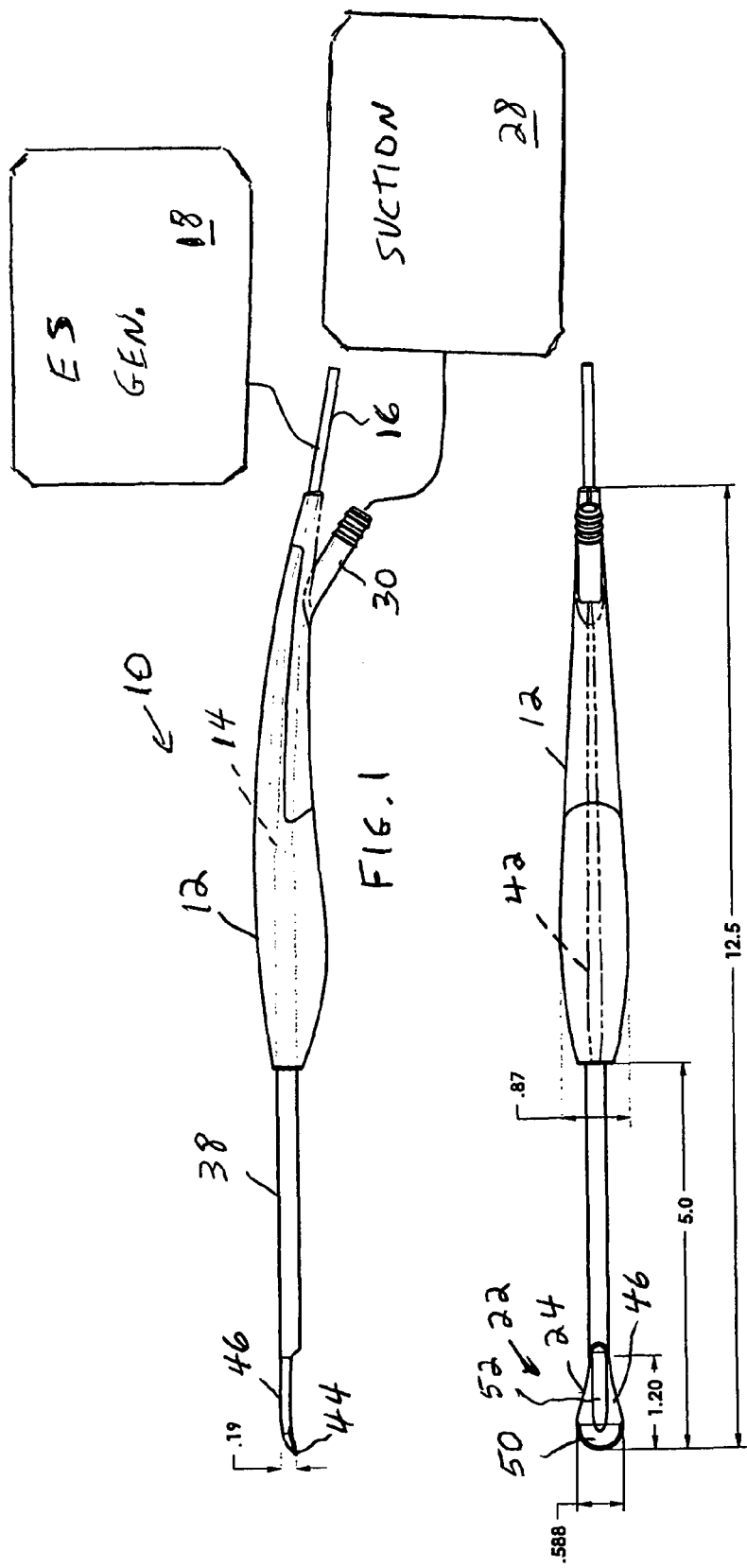

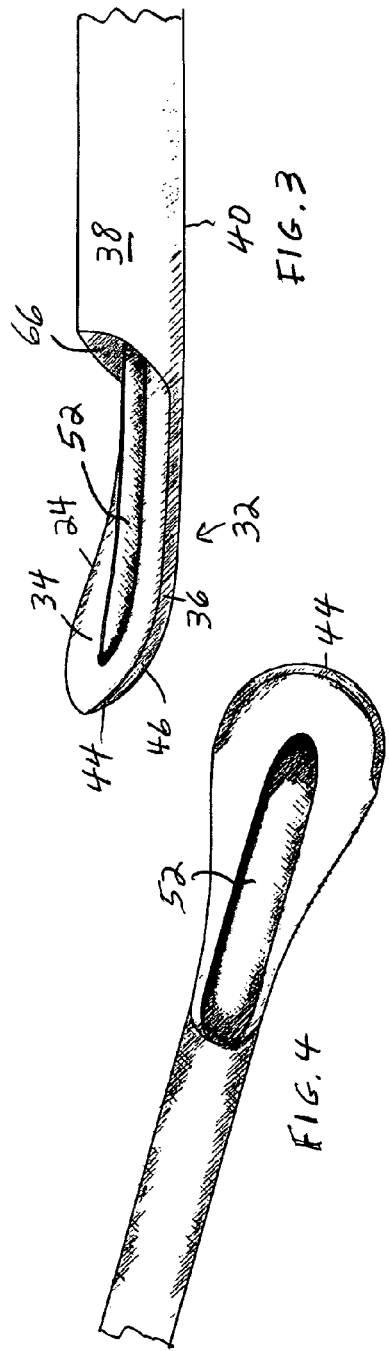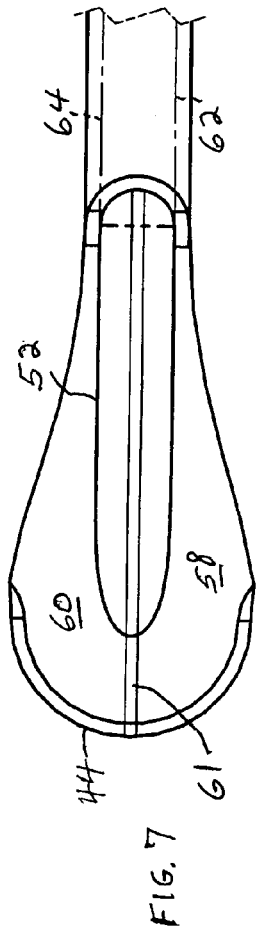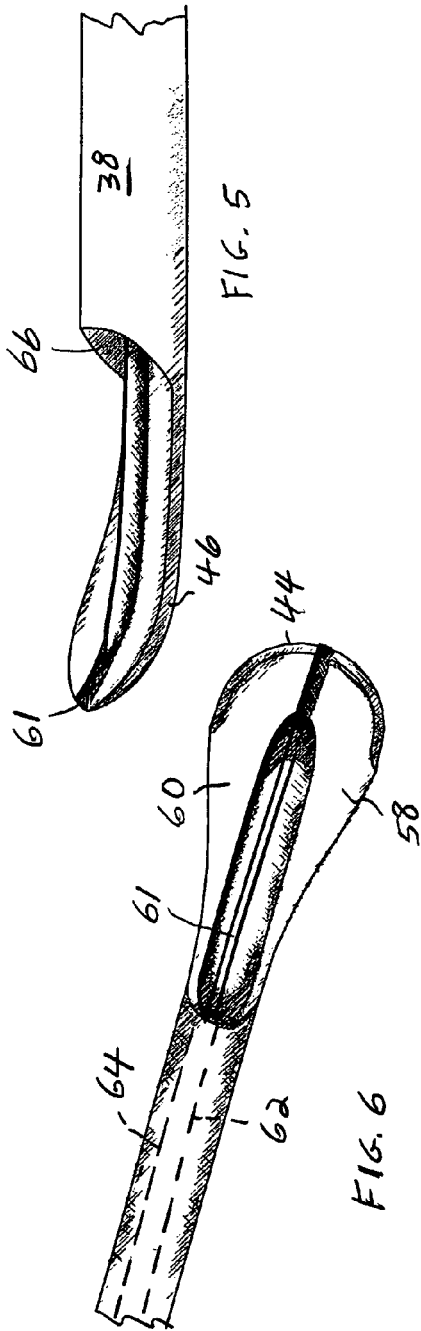

ELECTROSURGICAL COBB ELEVATOR INSTRUMENT

This invention relates to electrosurgery, and in particular to an improved Cobb elevator instrument that can also serve as an electrode for use in electrosurgical procedures which tend to produce vapors, odors or smoke plumes.

BACKGROUND OF THE INVENTION

Electrosurgery has become a common procedure for doctors. Electrosurgical handpieces are commercially available that will accommodate a wide variety of electrodes shapes and sizes, such as needles, blades, scalpels, balls and wire loops. Also, multi-function electrodes are available. It is also known that electrosurgical handpieces that can be connected to a source of electrosurgical energy can also be provided with a hollow tube with an exposed tip. By connecting a suction source to the hollow tube end, vapors and odors at the operative field can be drawn out.

Cobb elevator instruments are also known. A typical Cobb elevator consists of a smooth blade at the tip of an elongated handle. The blade is used to displace the tissue laterally, i.e., elevate the tissue from the bone. The Cobb elevator is also used to divide the muscle from the bone. In spinal and other surgery, a Cobb elevator is generally used by surgeons to retract tissue from the bone to which it is attached.

There are disadvantages associated with using the known Cobb elevator to retract tissue. One disadvantage is that a considerable effort is required on the part of the surgeon to displace the tissue, which can be tiring on the surgeon as the action basically involves blunt dissection. Another is that the Cobb elevator doesn't always firmly grasp the tissue and may slip. Moreover, the handle itself may slip in the grasp of the surgeon when firmly applied.

BRIEF SUMMARY OF THE INVENTION

An object of the invention is a surgical instrument of the Cobb elevator type that can safely dissect and/or retract tissue from bone during a surgical procedure.

A further object of the invention is a Cobb elevator instrument that not only can be used in the usual manual way for blunt dissection or tissue retraction, but that can be connected to use electrosurgical currents to aid in either the dissection or tissue retraction procedure greatly reducing the surgical effort required.

Still another object of the invention is a Cobb elevator instrument provided with a suction device integrated to an electrosurgical handpiece that is capable of providing efficient smoke removal and that is relatively inexpensive to manufacture.

According to one aspect of the invention, a Cobb elevator instrument comprises an elongated handle sufficiently large to accommodate a hand of a surgeon and having an active end in the shape of a spoon or cup capable of serving to elevate or retract tissue from bone during a medical procedure. The active instrument end is curved and the curved end is preferably sharpened and is constituted of electrically-conductive material. The latter is electrically connected by a wire or through an electrically-conductive handle part to the opposite handle end adapted to receive directly or indirectly an electrical cable that can be connected to an electrosurgical generator capable of providing radio-frequency (RF) electrosurgical currents, preferably in the range of 1-4 MHz.

In a preferred embodiment, a conduit for suction is integrated into the instrument in such manner that active suction via an exit aperture in the active end is active at the operative field. The opposite end of the handle is air-coupled via a suitable fitting to a suction source.

According to an aspect of the invention, the active electrode end is cup-shaped, preferably configured in the shape generally of a spoon, with an upper concave surface and an opposed lower convex surface and with the front edge exposed to provide electrosurgical currents to tissue.

The electrode front edge being sharp can be used to provide blunt dissection in the normal way in which surgeons manually use Cobb elevator instruments in many medical procedures. But, importantly, by activating the electrosurgical generator to which the instrument of the invention is connected, RF electrosurgical currents can be provided at the active edge providing electrosurgical energy-driven dissection. With electrosurgical energy-driven dissection, the effort required by the surgeon is greatly reduced. Moreover, by adjusting the electrosurgical currents, it is possible to obtain hemostasis of bleeders which normally occur during the tissue stripping. The resultant blood often obstructs the surgeon's vision, and thus stopping the blood aids in carrying out the procedure.

The resultant instrument that can be accurately described as an electrosurgical Cobb elevator instrument could be used in any medical procedure that requires soft tissue dissection and/or coagulation. This would be especially beneficial for many orthopedic surgeries such as spinal fusions and scoliosis, where the spinal column is stripped of tissue and readjusted with rods and screws, with subsequent fusion of bone graft up and down the spinal column for stabilization.

Other important applications would be total hip replacement, long bone fractures and total knee replacement surgeries or any other procedure with soft tissue and bone.

Preferably the handle is composed of an electrically-insulated material such as plastic, and an interior wire provided for electrically-connecting the electrically-conductive sharp edge to the cable end.

A suction conduit can be integrated into the electrode shank by using a hollow tube as the shank. The suction opening is preferably terminated at a groove in the upper concave surface close to the active curved edge.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described the preferred embodiments of the invention, like reference numerals or letters signifying the same or similar components.

BRIEF DESCRIPTION OF THE DRAWINGS

In the drawings:

FIG. 1 is a side view of one form of a monopolar electrosurgical Cobb instrument according to the invention shown schematically attached to an electrosurgical generator and suction source;

FIG. 2 is a top view of the electrosurgical Cobb instrument of FIG. 1;

FIG. 3 is an enlarged perspective view of the front end of a first variant of a monopolar electrosurgical Cobb instrument in accordance with the invention;

FIG. 4 is an enlarged perspective view of the front end of the first variant from a different angle;

FIG. 5 is an enlarged perspective view of the front end of a second variant of a bipolar electrosurgical Cobb instrument in accordance with the invention;

FIG. 6 is an enlarged perspective view from a different angle of the front end of the electrosurgical Cobb instrument of FIG. 5;

FIG. 7 is an enlarged top view of the front end of the electrosurgical Cobb instrument of FIG. 5.

DETAILED DESCRIPTION OF THE PREFERRED EMBODIMENTS

FIG. 1 is a side view and FIG. 2 is a top view of one form of a monopolar electrosurgical Cobb instrument 10 according to the invention. It comprises an elongated handle 12 sized to accommodate the hand of a surgeon and having internally a conduit 14 for suction and at its right end a cable 16 connected at its opposite end to a connector (not shown) for plugging into a standard electrosurgical generator 18 supplying electrosurgical currents to a working end 22 shaped in the form generally of a spoon 24. The cable 16 is electrically connected to the working end 22 so that when the electrosurgical generator 18 is switched on, electrosurgical currents are supplied to the working end 22. It is also common for an electrosurgical handpiece handle 12 to have finger switches (not shown) for remote operation of the electrosurgical generator. Such switches can be used but are not in the preferred embodiment of the invention as they could interfere with operation of the instrument 10 in certain procedures. Also shown in FIG. 1 are a source of suction 28 which may be selectively connected via a fitting 30 to the handpiece conduit 14 to supply suction to the front working end 22.

The electrosurgical generator preferably is a radiosurgical energy source. Studies have shown that high frequency combined with multiple outputs is the preferred RF energy to incise and coagulate tissue because tissue thermal necrosis is minimal. An example of a suitable electrosurgical generator is the Model SURGI-MAX electrosurgical unit manufactured by and available from Elliquence, LLC of Baldwin, N.Y. that supplies RF energy in the MHz range.

FIG. 3 is an enlarged perspective view of the front working end 32 of a monopolar variant of the of the FIG. 1 embodiment. As can be seen more clearly in that figure, the spoon-shaped part 24 has an upper concave surface 34 and an opposed lower convex surface 36. The spoon 24 is electrically-conductive, for example, of metal. The spoon 24 is connected to a hollow shank 38, which may also be of metal and is mounted to the handle 12 front end. The hollow shank 38 is in turn connected to the handle conduit 14, so a complete path for suction is provided throughout the handle and shank. The shank 38 is preferably covered with an electrically-insulated coating 40 to prevent shock to the surgeon when the generator 18 is turned on. The metal shank 38 is connected by an internal wire 42 to the cable 16 so that a complete electrical path is established to the metal spoon 24. Alternatively, the shank 38 can be of plastic and the internal wire extended through the shank to the spoon 24. The spoon 24, being constituted of one-piece metal, when electrically activated is thus a monopolar electrosurgical electrode. The curved leading edge 44 is preferably sharpened allowing the inactivated instrument to serve as a manual Cobb elevator. When the electrosurgical generator 18 is activated, then electrosurgical currents flow from the sharpened edge 44 to the tissue-bone interface providing energy-driven dissection.

In the first monopolar embodiment of FIGS. 1 and 2, the lower (back) surface 36 of the spoon 24 is coated with an electrically-insulated coating 46, and the rear portion of the upper surface, up to the line 48, is similarly coated with an electrically-insulated coating 46. Thus the only electrically active part of the spoon 24 is the exposed part 50 in front including the sharpened edge 44. This focuses the electrosurgical currents to the front edge 44 which is applied by the surgeon to the tissue-bone interface where the tissue retraction is to occur. The hollow shank 38 terminates at an axially-extending groove 52 in the spoon's upper surface 34 which this directs the suction to the surgical site to remove any smoke or plume formed when electrosurgical currents are active. The active edge or tip of the working end spoon can also be configured as a knife blade, chisel, or other types of tip designs; including serrated uneven edges, capable of tissue dissection or tissue retraction. The monopolar variant of FIGS. 3 and 4 differs in that, while the electrically-insulated coating 46 is still present on the lower convex spoon surface, the electrically-insulated coating has been omitted from the upper concave spoon surface. This variant is thus somewhat easier to manufacture but requires somewhat more care by the surgeon to avoid undesirable electrical contact with the exposed upper surface when the generator is activated.

FIGS. 5 to 7 show a bipolar variant of the electrosurgical Cobb elevator of the invention. It differs from the monopolar embodiment in that the spoon 56 is split axially into two electrically-insulated segments 58, 60 by a thin electrically-insulating layer 61. This bipolar arrangement is similar to the two split half balls described in the bipolar embodiment of U.S. Pat. No. 6,231,571. Thus, as in the patent, each of the spoon segments must be connected to its own separate electrical wire 62, 64 extending through the shank and handle to the cable which in turn is now plugged into the bipolar socket of the generator. When operated with electrosurgical currents, the currents are thus focused and confined between the bipolar front edges 58, 60. As before, the lower convex surface has an electrically-insulated coating 46. The operation is otherwise similar to the monopolar embodiments.

In the electrical operation of the system, with the suction source 28 attached to the handpiece 10, when the suction generator is activated, the reduced pressure is conveyed down the hollow conduit 14, into and through the hollow shank 38, and escapes via the port 66 at the exit of the shank 38, and is thereupon conducted via the groove 52 which it will be noted is always located very close to the point of origin of any smoke/plume, which is where the sharpened edge 44 excises the tissue when the electrosurgical generator is activated. This allows smoke and airborne contaminants to be captured close to their point of origin, and avoids the need of an additional staff member to hold a separate plume capture device near the excision site.

The electrosurgical Cobb elevator instrument of the invention has dimensions similar to a manual Cob elevator. Some typical dimensions are illustrated in FIGS. 1 and 2. The dimensions shown are not critical. For example, the overall instrument length (the typical shown value being 12.5") can vary between about 8-16 inches long; the shank length (the typical shown value being 5") can vary between about 3-7 inches long; the typical handle 12 length is about 3-5 inches to accommodate the hand of the surgeon; the length of the spoon 22 (the typical shown value being 1.2") can vary between about 0.8-2 inches long; the spoon width (the typical shown value being 0.588") can vary between about 0.3-0.8 inches wide; the height of the spoon (the typical shown value being 0.19") can vary between about 0.12-2.4 inches high. The drawing of FIGS. 1 and 2 is to scale so that other dimensions can readily be derived.

The spoon end may be of stainless steel or brass. The electrically-insulated coating may be of Teflon or other plastic or ceramic.

The soft tissue dissection tool of the invention can be used with and without suction, and is capable of delivering monopolar and/or bipolar radiowave energy for cutting and coagulating soft tissue. The device is capable of footswitch or handswitch activation. If desired, the handle can be configured to allow for the spoon/shaft combination to be changed for different style and size electrodes. The spoon edge is preferably sharp to provide blunt dissection in addition to the energy-driven dissection.

The instrument of the invention could be used in any procedure that requires soft tissue dissection and/or coagulation. For example, this would be beneficial for scoliosis, as the spinal column is stripped of tissue and readjusted with rods and screws, with subsequent fusion of bone graft up and down the spinal column for stabilization.

For the monopolar modality, the sharp dissection exposed edge can be energized to provide cutting and coagulation.

For the bipolar modality, the sharp dissection exposed edge can be split to provide active and return poles for the energy to pass confined to the region between the poles to provide cutting and coagulation.

Other variations in the shape of the instrument's working end while retaining its benefits and advantages will be evident to those skilled in the art.

To summarize, the main purpose or intent in any procedure using the electrosurgical Cobb electrode according to the invention is to dissect, namely, carefully and precisely separate any tissue from its bone. A second important point would be hemostasis control. A third goal is to reduce unwanted tissue necrosis, by limiting the electrosurgical energy to remove only the desired tissue and prevent the electrosurgical energy from affecting the surrounding healthy tissue. A fourth point is to remove the smoke plume, which results from the dissection of the tissue. This actually accomplishes several important advantages. It visually clears the surgical sight for the surgeon and it prevents the plume from traveling to the nose and throat of the patient or the surgeon. The instrument of the invention satisfies these four important aspects of the surgical procedure in a relatively simple and inexpensive manner.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. An electrosurgical instrument, comprising:
   an axially elongated body being detachably connectable to an electrosurgical generator at a first end of the axially elongated body, wherein the axially elongated body has an active electrosurgical end at a second end of the axially elongated body;
   an internal path of the axially elongated body electrically connecting the active electrosurgical end and the first end, wherein the internal path is capable of supplying electrosurgical currents to a patient tissue when the first end of the axially elongated body is connected to the electrosurgical generator;
   a spoon-shaped portion extending from the active electrosurgical end in a direction away from the axially elongated body, wherein the spoon-shaped portion comprises a concave upper surface and a convex lower surface on an opposite side of the concave upper surface;
   an edge extending from the spoon-shaped portion capable of elevating and displacing the patient tissue from a bone when the edge extending from the spoon-shaped portion is applied to a patient tissue edge and pulled by a surgeon along the bone;
   wherein the concave upper surface has a substantially smooth and curved shape adapted to direct the patient tissue away from the bone;
   an exposed groove recessed into the concave upper surface and extending axially along the concave upper surface from the active electrosurgical end and terminating at an end position before reaching the edge extending from the spoon-shaped portion; and
   a conduit extending through the axially elongated body from the first end to the second end, wherein the exposed groove is axially aligned with the conduit, wherein the conduit and the exposed grove are capable of establishing suction at the concave upper surface of the spoon-shaped portion to remove materials that form during removal of the patient tissue;
   wherein the exposed groove extends axially with respect to a longitudinal axis of the axially elongated body, wherein the end position of the exposed groove is located at a most distal position from the axially elongated body with respect to a remainder of the exposed groove;
   wherein the spoon-shaped portion has a transverse width across the spoon-shaped portion, wherein the exposed groove extends for a longer distance along the longitudinal axis than the transverse width;
   wherein the edge extending from the spoon-shaped portion has a distal edge portion that is perpendicular to the longitudinal axis, wherein the distal edge portion is located at a most distal point from the axially elongated body with respect to a remainder of the edge extending from the spoon-shaped portion; and
   wherein the end position of the exposed groove is located on the spoon-shaped portion between the distal edge portion of the spoon-shaped portion and the transverse width such that the exposed groove does not intersect the distal edge portion of the spoon-shaped portion or the edge extending from the spoon-shaped portion.

2. The electrosurgical instrument as set forth in claim 1, wherein:
   the active electrosurgical end is a monopolar electrode;
   the spoon-shaped portion is solid and the concave upper surface and the convex lower surface are coated with an electrically-insulating layer; and
   the edge of the spoon shaped portion is free of the electrically-insulating layer.

3. The electrosurgical instrument as set forth in claim 2, wherein the axially elongated body is sized to accommodate a hand of the surgeon.

4. The electrosurgical instrument as set forth in claim 2, wherein an overall length of the electrosurgical instrument is about 8 to 16 inches long.

5. The electrosurgical instrument as set forth in claim 2, wherein:
   the edge extending from the spoon-shaped portion forms substantially a ninety degree semicircle; and
   each of two end portions of the semicircle connect to the active electrosurgical end along slightly concave regions of the spoon-shaped portion.

6. The electrosurgical instrument as set forth in claim 2, wherein the exposed grove is shaped substantially as a half cylindrical groove that slopes flush with the concave upper surface at a location proximate the edge extending from the spoon-shaped portion.

7. The electrosurgical instrument as set forth in claim 6, wherein the conduit is cylindrical.

8. The electrosurgical instrument as set forth in claim 1, wherein the exposed grove:

is shaped as a smooth trough oriented axially with respect to a horizontal axis of the axially elongated body;
is substantially flush with the concave upper surface at the most distal position from the axially elongated body; and
is substantially semi-cylindrical and axially aligned with the conduit at a position proximate the conduit such that the exposed groove channels the materials from the edge extending from the spoon-shaped portion to the conduit.

* * * * *